(12) United States Patent
Brandt et al.

(10) Patent No.: US 6,183,989 B1
(45) Date of Patent: Feb. 6, 2001

(54) PROCESS FOR MAKING DESIRED POLYPEPTIDES IN YEAST

(75) Inventors: Jacob Brandt, Bronshoj; Knud Vad, Vanlose, both of (DK)

(73) Assignee: Novo Nordisk A/S, Bagsvaerd (DK)

( * ) Notice: Under 35 U.S.C. 154(b), the term of this patent shall be extended for 0 days.

(21) Appl. No.: 09/261,853

(22) Filed: Mar. 3, 1999

Related U.S. Application Data

(63) Continuation of application No. PCT/DK99/00031, filed on Jan. 22, 1999
(60) Provisional application No. 60/076,882, filed on Mar. 5, 1998.

(30) Foreign Application Priority Data

Jan. 23, 1998 (DK) .................................................. 0098-98

(51) Int. Cl.$^7$ .............................. C12P 21/06; C12P 21/04
(52) U.S. Cl. ......................................... 435/69.1; 435/69.9
(58) Field of Search .................................... 435/69.1, 69.9

(56) References Cited

U.S. PATENT DOCUMENTS 5,591,640   1/1997   Loison et al. ..................... 435/320.1

FOREIGN PATENT DOCUMENTS

| 0 324 274 | 7/1989 | (EP) . |
|---|---|---|
| WO 90/10075 | 9/1990 | (WO) . |
| WO 90/13653 | 11/1990 | (WO) . |
| WO 92/11378 | 7/1992 | (WO) . |
| WO 95/34666 | 12/1995 | (WO) . |
| WO 95/35384 | 12/1995 | (WO) . |
| WO 98/28429 | 7/1998 | (WO) . |

OTHER PUBLICATIONS

Bird, P, Gething, M–J, Sambrook, J. (1987) "Translocation in Yeast & Mammalian Cells;" 105: 2905–2914, (Dec. 1987).*
Latchinian–Sadek, L., Thomas, D. (1993) "Expression, Purification & Characterization of the Yeast KEXI Gene Product," JBC 268: 534–40, Jan. 1993.*
Baba et al., Biochem. and Biophy. Res. Comm., vol. 184, No. 1, pp. 50–59 (1992).
Kjeldsen et al., Gene , vol. 170, pp. 107–112 (1996).
Clements et al., Gene, vol. 106, pp. 267–272 (1991).
Chaudhuri et al., Eur. J. Biochem., vol. 210, pp. 811–822 (1992).
Sleep et al., Bio/Tech., vol. 8, pp. 42–46 (Jan. 1990).
Bourbonnais et al., Journal of Biological Chemistry, vol. 266, No. 20, pp. 13203–13209 (Jul. 15, 1991).
Seeboth et al., Appl. Microbiol. Biotechnol. vol. 35, pp. 771–776 (1991).
Julius et al., Cell., vol., 37, pp. 1075–1089, (Jul. 1984).

* cited by examiner

Primary Examiner—Robert S. Schwartman
Assistant Examiner—Katharine F Davis
(74) Attorney, Agent, or Firm—Steve T. Zelson, Esq.; Valeta A. Gregg, Esq.

(57) ABSTRACT

The invention describes a process for making desired polypeptides in yeast. The desired products are expressed as leader bound polypeptides connected by means of a monobasic processing site. The desired polypeptide is cleaved from the leader either in vivo or in vitro by enzymatic cleavage.

11 Claims, 1 Drawing Sheet

SEQUENCE LISTING

<160> NUMBER OF SEQ ID NOS: 9

<210> SEQ ID NO 1
<211> LENGTH: 83
<212> TYPE: PRT
<213> ORGANISM: Yeast

<400> SEQUENCE: 1

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp

<210> SEQ ID NO 2
<211> LENGTH: 53
<212> TYPE: PRT
<213> ORGANISM: Yeast

<400> SEQUENCE: 2

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Ala Ala Lys
             20                  25                  30

Gly Ile Val Glu Gln Cys Cys Thr Ser Ile Cys Ser Leu Tyr Gln Leu
         35                  40                  45

Glu Asn Tyr Cys Asn
     50

<210> SEQ ID NO 3
<211> LENGTH: 32
<212> TYPE: PRT
<213> ORGANISM: Yeast

<400> SEQUENCE: 3

His Ala Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Gly Arg Gly Lys
             20                  25                  30

<210> SEQ ID NO 4
<211> LENGTH: 5
<212> TYPE: PRT
<213> ORGANISM: Yeast

<400> SEQUENCE: 4

Lys Lys Leu Ile Asp
 1               5

<210> SEQ ID NO 5
<211> LENGTH: 4
<212> TYPE: PRT
<213> ORGANISM: Yeast

<400> SEQUENCE: 5

Pro Gly Asp Pro
 1

<210> SEQ ID NO 6
<211> LENGTH: 5
<212> TYPE: PRT
<213> ORGANISM: Yeast

<400> SEQUENCE: 6

Lys Lys Leu Ile Asp
 1               5

<210> SEQ ID NO 7
<211> LENGTH: 4
<212> TYPE: PRT
<213> ORGANISM: Yeast

<400> SEQUENCE: 7

Pro Gly Asp Pro

-continued

```
<210> SEQ ID NO 8
<211> LENGTH: 7
<212> TYPE: PRT
<213> ORGANISM: Yeast

<400> SEQUENCE: 8

Lys Glu Ala Glu Ala Glu Ala
 1               5

<210> SEQ ID NO 9
<211> LENGTH: 8
<212> TYPE: PRT
<213> ORGANISM: Yeast

<400> SEQUENCE: 9

Lys Glu Ala Glu Ala Glu Ala Lys
 1               5
```

PROCESS FOR MAKING DESIRED POLYPEPTIDES IN YEAST

CROSS-REFERENCE TO RELATED APPLICATIONS

This is a continuation application of PCT/DK99/00031 filed Jan. 22, 1999 and claims priority under 35 U.S.C. 119 of Danish application 0098/98 filed Jan. 23, 1998 and U.S. provisional application Ser. No. 60/076,882 filed Mar. 5, 1998, the contents of which are fully incorporated herein by reference.

FIELD OF THE INVENTION

The present invention relates to a process for making desired polypeptides in yeast by expressing fusion polypeptides containing a monobasic protease processing site.

Background of the Invention

Yeast organisms produce a number of proteins synthesized intracellularly, but having a function outside the cell. These extracellular proteins are referred to as secreted proteins. Initially the secreted proteins are expressed inside the cell in the form of a precursor or a pre-protein containing a pre-peptide sequence ensuring effective direction of the expressed product (into the secretory pathway of the cell) across the membrane of the endoplasmic reticulum (ER). The pre-sequence, normally referred to as a signal peptide, is generally cleaved off from the desired product during translocation. Once having entered the secretory pathway, the protein is transported to the Golgi apparatus. From the Golgi apparatus the proteins are distributed to the plasma membrane, lysosomes and secretory vesicles.

Several approaches have been suggested for the expression and secretion in yeast of proteins heterologous to yeast. European published patent application No. 116 201 describes a process by which proteins heterologous to yeast are expressed, processed and secreted by a yeast host transformed by an expression vehicle harboring DNA encoding the desired protein, a leader sequence and a processing signal, preparing a culture of the transformed organism, growing the culture and recovering the protein from the culture medium, the leader sequence being a yeast α-factor leader sequence.

The *Saccharomyces cerevisiae* MFα1 (α-factor) is synthesized as a pre-pro form of 165 amino acids comprising a signal or prepeptide of 19 amino acids followed by a "leader" or propeptide of 64 amino acids, encompassing three N-linked glycosylation sites followed by (LysArg ((Asp/Glu)Ala)$_{2-3}$ α-factor)$_4$ (Elements et al., Gene, 106, 1991, pp. 267–272). This publication describes certain modifications of the KEX2 site with the purpose of improving the KEX2 processing.

The signal-leader part of the pre-pro MFα1 has been widely employed to obtain synthesis and secretion of heterologous proteins in *S. cerevisiae*.

European published patent application No. 301 669 describes a process by which leader-sequences, in particular α-factor leaders, are directing the secretion of expressed α-factor leaders, are directing the secretion of expressed heterologous polypeptides in yeast. EP 324 274 discloses an improvement in the efficiency of expression and secretion of heterologous polypeptides by truncating the glycosylated a-factor leader sequence.

The secreted polypeptides are routed so as to be exposed to a proteolytic processing system which cleaves the peptide bond at the carboxy end of two consecutive basic amino acid residues. This enzymatic activity is in *S. cerevisiae* encoded by the KEX2 gene (Julius, D. A. et al., GENE, 37, 1884b, pp. 1075). Processing of the product by the KEX2 protease is necessary for the secretion of active *S. cerevisiae* mating factor α1 (MFα1 or α-factor) whereas KEX2 is not involved in the secretion of *S. cerevisiae* mating factor a.

WO 90/10075 and WO 95/35384 describe modifications around the KEX2 site. Furthermore WO 95/34666, WO 92/11378 and WO 90/13653 describe the option of utilizing a secondary processing site comprised of the amino acids Ile-Glu-Gly-Arg named FX$_a$, in situations where the usage of KEX2 is impractical.

In Applied Microbiological Biotechnology 35 (1991) 771–776, Seeboth et al., describes a mechanism by which a-leader bound polypeptides in yeast are processed by soluble KEX2 in vitro, wherein KEX2 was made soluble by modifying the KEX2 gene, and thereby presenting a method of increasing the site-specific processing in vitro. In GENE, 170 (1996) 107–112, Kjeldsen et al. describe that insertion of a spacer peptide following the dibasic KEX2 site, creating a N-terminal extension of the polypeptide precursor, greatly facilitates the KEX2 processing and subsequently improves the yield of the polypeptide precursor.

A recognized problem with the above described processes is that the level of secretion may be too low or the proteolytic processing may be incorrect or incomplete resulting in lower yields of the desired product.

The object of the present invention is to provide a yeast expressing process ensuring high yields of a desired polypeptide.

SUMMARY OF THE INVENTION

This invention relates to a process for making a desired polypeptide in yeast by expressing and secretion of a leader bound polypeptide which does not contain a KEX2 processing site. The leader bound polypeptide comprises the native a-factor leader peptide and the desired polypeptide linked by a monobasic processing site and possibly a spacer peptide.

More specifically, the present invention is related to a process of making a desired polypeptide in yeast by culturing in a suitable culture medium a yeast strain containing an expression vector capable of expressing a sequence with the following formula SP-LP-X$_n$-PS-*polypeptide* wherein
SP is a signal peptide;
LP is the native α-factor leader peptide or a leader peptide being at least 85% homologue to the native α-factor leader peptide;
PS is a monobasic processing site Lys or Arg;
X is a spacer peptide containing n amino acids;
n is 0 or an integer from 1 to 10; and
*polypeptide* is the desired polypeptide;
with the proviso that the spacer peptide X is not Ile-Glu-Gly, Leu-Pro, Lys-Lys-Leu-Ile-Asp (SEQ ID NO: 4), Ile-Asp or Pro-Gly-Asp-Pro (SEQ ID NO: 5) and with the further proviso that the spacer peptide X does not contain a KEX2 cleavage site or together with PS or LP constitutes a KEX2 cleavage site and, when n=0, the C-terminal of the leader peptide is not Lys, Arg, Ile-Glu-Gly, Leu-Pro, Lys-Lys-Leu-Ile-Asp (SEQ ID NO: 6), Ile-Asp or Pro-Gly-Asp-Pro (SEQ ID NO: 7), whereupon the leader bound polypeptide is cleaved at the processing site PS either in vivo during passage through the cell membrane or in vitro after secretion into the culture medium whereupon the desired polypeptide is isolated.

The present invention also relates to DNA sequences encoding the above leader bound polypeptide, expression vectors containing such DNA sequences and yeast strains transformed with such vectors.

BRIEF DESCRIPTION OF THE DRAWINGS

The present invention is illustrated with reference to the attached drawing wherein.

Figure 1:
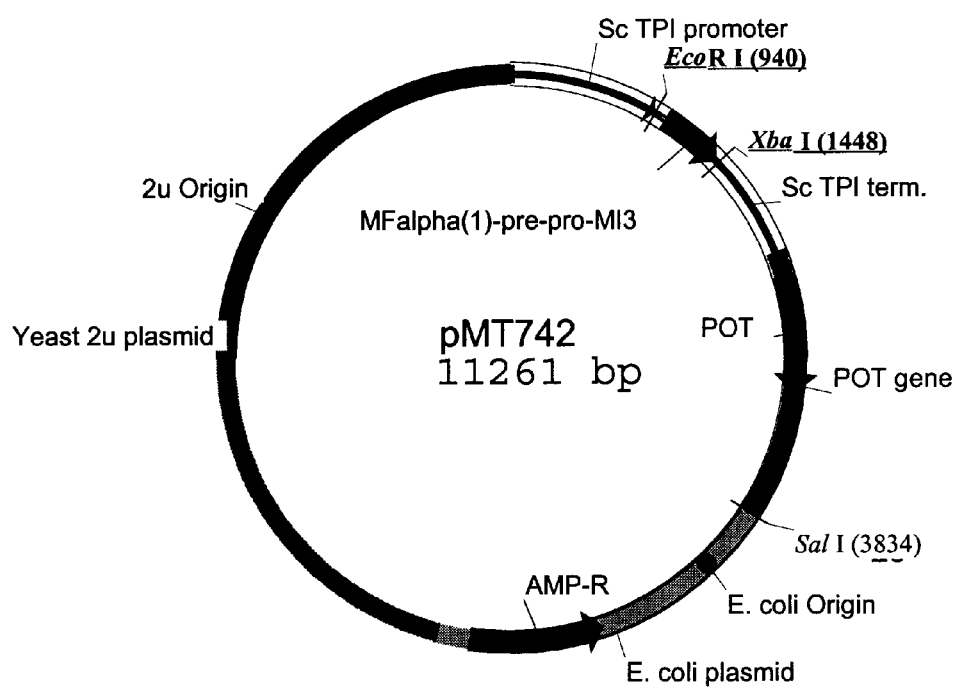
FIG. 1 is a schematic illustration of the yeast expression plasmid pMT742. This plasmid contains a gene for expression of MFαl pre-pro-(1-85)-MI3.

The following symbols are used:
Sc TPI promoter: Triose phosphate isomerase (TPI) gene promoter sequence from *Saccharomyces cerevisiae* (Sc).
Sc TPI term.: TPI gene terminator sequence from Sc.
POT gene: TPI gene from *Schizosaccharomyces Pombe*.
POT: Sequence encoding TPI from *S. Pombe*.
*E. coli* plasmid: Sequence derived from plasmid pBR322 and pUCI3 an origin of replication.
AMP-R: Sequence encoding β-lactamase (ampicillin resistance marker).
Yeast 2u plasmid: sequences from Sc 2μ plasmid including its origin of replication.

DETAILED DESCRIPTION OF THE INVENTION

The leader peptide (LP) used in the present invention is preferably the native α-factor leader peptide, that is the propeptide of MFαl(1-83) (SEQ ID NO: 1). In MFαl (1-83), residues 1–19 form the so-called pre sequence or signal peptide and residues 20–83 form the so-called pro sequence or leader peptide.

The native α-factor leader peptide may by slightly modified by well known techniques whereby a few amino acid residues are deleted or substituted with other amino acid residues. The leader may thus be modified at the C terminal end where from 2 to 5 amino acid residues may be substituted with other amino acid residues to improve processing at the processing site PS. Preferably, the modified leader sequence will be more than 85% homologous and more preferably more than 90% homologous to the native a-factor leader peptide based on amino acid composition.

In a preferred embodiment the last two amino acid residues at the C terminal end of the α-factor leader peptide are substituted with Met-Ala.

The signal peptide used in the present invention can be any peptide ensuring safe and efficient guidance of the expressed polypeptide when entering the secretory pathway. The term "signal peptide" must be understood as a prepeptide sequence having the function of safely directing the expressed polypeptide across the membrane of the endoplasmatic reticulum where the signal peptide is cleaved off during translocation. The signal peptide may be homologous to yeast or it can be heterologous to yeast. It may be a naturally occurring or synthetic signal sequence. The signal peptide is situated N-terminally of the leader sequence and is predominantly hydrophobic in nature. Preferably SP is a DNA sequence encoding a a-factor signal peptide. Suitable other signal peptides are the yeast aspartic protease 3 signal peptide, the mouse salivary amylase signal peptide, the carboxypeptidase signal peptide and the yeast BAR1 signal peptide.

According to present invention cleavage of the leader bound polypeptide at the processing site PS is done by means of a protease specific for monobasic processing sites (Lys, Arg). Examples of such proteases are trypsin, *Achromobacter lyticus* protease I, Enterokinase, and *Fusarium oxysporum* trypsin-like protease. A preferred protease is yeast aspartyl protease 3 (YAP3).

The cleavage of the leader bound polypeptide from the leader peptide may be conducted in vitro after secretion of the leader bound polypeptide. The cleavage may be conducted by addition of a suitable protease to the culture medium followed by isolation of the desired polypeptide. As an alternative, the leader bound polypeptide may be isolated from the culture medium and cleaved after isolation.

Alternatively, the cleavage takes place in vivo by co-expression of a protease specific for the monobasic protease site PS.

The desired polypeptide may be any polypeptide capable of being expressed in a yeast cell and may be selected from the group consisting of aprotinin, tissue factor pathway inhibitor or other protease inhibitors, Insulin-like growth factor I or II, human or bovine growth hormone, Interleukin, tissue plasminogen activator, glucagon, glucagon-like peptide-1, Factor VII, Factor VIII, Factor XIII, plateletderived growth factor and industrial enzymes, and any functional analogue thereof. Preferably, the polypeptides are insulin, insulin analogues, precursors of insulin and insulin analogues, insulin like growth factors, or functional analogues thereof.

The polypeptides may also be the smaller human peptides of the proglucagon family, such as glucagon GLP-1, GLP-2 and GRPP including truncated forms, such as GLP-1 (7-37) and GLP-1 (7-36) or functional analogues thereof, such as GLP1*.

The term "functional analogue" indicates a polypeptide functionally equivalent to the native polypeptide, but having a modification compared to the native polypeptide.

The functional analogue may differ from the native polypeptide by having one or more amino acids deleted, truncated, substituted, or inserted. Amino acids may be deleted, truncated, substituted, or inserted within the sequence, or at the C-terminal end, or at the N-terminal end, or at both, or all of the above sites.

An example of an insulin precursor is MI3 with the structure B(1-29)-Ala-Ala-Lys-A(1-21) where B(1-29) is the B chain of human insulin lacking the amino acid residue in position B(30) and A(1-21) is the A chain of human insulin.

The function of the spacer peptide X is to optimize the cleavage of the leader from the desired polypeptide at the processing site PS. It is of importance that neither the leader peptide (LP) nor the spacer peptide (X) contain a KEX2 processing. Without being bound by theory it is believed that the presence of a KEX2 site in the leader peptide or in the spacer peptide would reduce the yield of secreted product due to premature cleavage in the secretory pathway.

The spacer sequence X may be any polypeptide sequence with up to 10 amino acid residues (n=10) as long as it does not contain a KEX2 site or together with the monobasic processing site PS or the leader peptide LP forms a KEX2 site. X will preferably contain 7 (n=7) and more preferably 2 (n=2) amino acid residues. In a preferred embodiment X is Lys-Glu-Ala-Glu-Ala-Glu-Ala (SEQ ID NO: 8) or Lys-Glu.

In another preferred embodiment n is zero meaning that there is no spacer sequence between the leader (LP) and the monobasic processing site (PS). In that case, the C terminal end of the leader peptide must not constitute a KEX2 site or a KEX2 like site nor must the C-terminal amino acid residue together with PS form a KEX2 site.

The yeast cell used in the present process may be selected from the group consisting of *Saccharomyces uvae, Saccharomyces kluyveri, Schizosaccharomyces pombe, Saccharomyces uvarum, Kluyveromyces lactis, Hansenula polymorpha, Pichia pastoris, Pichia methanolica, Pichia kluyveri, Yarrowia lipolytica*, Candida sp., *Candida utilis, Candida cacaoi*, Geotrichum sp. and *Geotrichum fermentans*. The preferred yeast strain is *Saccharomyces cerevisiae*.

The yeast cell may be transformed with a gene encoding a protease specific for monobasic processing sites, thereby obtaining a co-expression of protease and the desired polypeptide.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. The DNA constructs may be prepared synthetically by established standard methods, e.g., the phosphoamidite method described by S. L. Beaucage and M. H. Caruthers, *Tetrahedron Letters* 22, 1981, pp. 1859–1869, or the method described by Matthes et al., *EMBO Journal* 3, 1984, pp. 801–805. According to the phosphoamidite method, oligonucleotides are synthesized, e.g., in an automatic DNA synthesizer, purified, duplexed and ligated to form the synthetic DNA construct. A currently preferred way of preparing the DNA construct is by polymerase chain reaction (PCR), e.g., as described in Sambrook et al., *Molecular Cloning: A Laboratory Manual*, Cold Spring Harbor, N.Y., 1989).

The expression vector which may be linear or circular will comprise the DNA sequence encoding the desired polypeptide operably linked to additional segments that provide for its transcription. Such additional segments may include promoter and terminator sequences, and optionally one or more origins of replication, one or more selectable markers, an enhancer, a polyadenylation signal, and the like.

Suitable yeast promoters are the MFα1 promoter, galactose inducible promoters such as GAL1, GAL7 and GAL10 promoters, glycolytic enzyme promoters including TPI and PGK promoters, TRP1 promoter, CYCI promoter, CUP1 promoter, PHO5 promoter, ADH1 promoter, and HSP promoter. Other useful promoters for yeast host cells are described by Romanos et al., 1992, Yeast 8:423–488.

The expression vector will also typically contain a terminator operably linked to the 3' terminus of the nucleic acid sequence encoding the desired polypeptide. Any terminator which is functional in the yeast cell may be used in the present invention.

Preferred terminators will be derived from the genes encoding *Saccharomyces cerevisiae* enolase, *Saccharomyces cerevisiae* cytochrome C (CYC1), or *Saccharomyces cerevisiae* glyceraldehyde-3-phosphate dehydrogenase, triosephosphate isomerase and mating factor MFα1, or from *S. kluyveri* glycolytic and respiratory genes. Other useful terminators for yeast host cells are described by Romanos et al., 1992, supra.

The vector will preferably contain one or more selectable markers which permit easy selection of transformed cells. A selectable marker is a gene the product of which provides for biocide or viral resistance, resistance to heavy metals, prototrophy to auxotrophs, and the like. Suitable markers for yeast host cells are ADE2, HIS3, LEU2, LYS2, MET3, TRP1, URA3, TPI1, PGK and geneticin G418$^R$ by the KAN$^{E.c.}$ gene.

For autonomous replication, the vector will further comprise an origin of replication enabling the vector to replicate autonomously in the yeast host. Examples of origin of replications for use in a yeast host cell are the 2 micron origin of replication, the combination of CEN6 and ARS4, and the combination of CEN3 and ARS1. The origin of replication may be one having a mutation which makes its functioning temperature-sensitive in the host cell (see, e.g., Ehrlich, 1978, Proceedings of the National Academy of Sciences USA 75:1433).

The preferred yeast expression vectors are plasmids characterized by the presence of the *Schizosaccharomyces pombe* triose phosphate isomerase (POT) gene. The POT gene is used for the selection of transformants and will also ensure maintenance of the plasmids in a triose phosphate isomerase (TPI) negative *Saccharomyces cerevisiae* strain.

The procedures used to ligate the elements described above to construct the recombinant expression vectors of the present invention are well known to one skilled in the art (see, e.g., Sambrook et al., 1989, supra).

The yeast strain may be transformed using the procedures described by Becker and Guarente, In Abelson, J. N. and Simon, M. I., editors, Guide to Yeast Genetics and Molecular Biology, Methods in Enzymology, Volume 194, pp 182–187, Academic Press, Inc., New York; Ito et al., 1983, Journal of Bacteriology 153:163; and Hinnen et al., 1978, Proceedings of the National Academy of Sciences USA 75:1920.

The transformed yeast host cells are then cultured for a sufficient time and under appropriate conditions known to those skilled in the art in view of the teachings disclosed herein to permit the expression and secretion of the desired product.

The product is isolated and purified by methods well known within the art. If the secreted and isolated product is a precursor for an active polypeptide, such as an insulin precursor, the precursor is converted into the active polypeptide by known means such as enzymatic conversion.

Throughout the description and claims is used one and three letter codes for amino acids in accordance with the rules approved (1974) by the IUPAC-IUB Commission on Biochemical Nomenclature, vide Collected Tentative Rules & Recommendations of the Commission on Biochemical Nomenclature IUPAC-IUB, 2nd ed., Maryland, 1975.

The invention is further exemplified by the following examples:

EXAMPLE 1

Cloning and generation of leader/product fusions in *S. cerevisiae*.

In the present studies the yeast expression plasmid of the episominally derived POT type (Thim et al., PNAS 83, 1986, pp. 6766–6770; Kjeldsen et al., Gene 170, 1996, pp.107–112; PCT No. 95/00250 and PCT No. 97/00298) was used.

FIG. 1 shows an example of a yeast plasmid called pMT742 (Egel-Mitani et al., Gene, 73, 1988, pp.113–120). The plasmid contains an expression cassette comprising an EcoRI-XbaI fragment inserted into the plasmid between the transcription-promoter and the transcription-terminator of the *S. cerevisiae* TPI gene.

In plasmid pMT742 the EcoRI-XbaI fragment encodes a fusion product composed of the MFα1 pre-pro leader, a Lys-Arg cleaving site for the dibasic processing endopeptidase KEX2, and the single-chain mini-insulin precursor MI3.

In order to construct plasmids encoding various leader/product fusions (see Table 1), modifications were introduced between the EcoRI and the XbaI site by the techniques of PCR or overlap PCR, using appropriate oligonucleotides, followed by isolation and cloning using standard molecular methods (e.g. Sambrook, J., Fritsch, E. F. and Maniatis, T., *Molecular Cloning: A Laboratory Manual*, Cold Spring Harbour 10 Laboratory Press, New York, 1989) as outlined in PCT patent application no. 95/00250.

Table 1 shows different plasmid constructs of leader/product fusions

TABLE 1

Plasmid Constructs
Leader/product fusion encoded by the
EcoRI-XbaI fragment

| Plasmid | Pre-pro leader | Spacer and processing site.[a] | Gene | Co-expressed protease |
|---|---|---|---|---|
| pMT742 | MFα1(1-83) | Lys-Arg (comparison) | MI3 | ÷ |
| pJBI62 | MFα1(1-83) | Lys (= n = 0) | MI3 | ÷ |
| pJB 160 | MFα1( 1-81 )MA | Lys-Glu-Ala-Glu-Ala-Glu-Ala-Lys (SEQ ID NO:9) | MI3 | ÷ |
| pIM 176 | MFα1( 1-81 )MA | Lys-Glu-Ala-Glu-Ala-Glu-Ala-Lys (SEQ ID NO:9) | MI3 | YAP3 |
| pIM37 | MFα1(1-81)MA | Lys-Glu-Ala-Glu-Ala-Glu-Ala-Lys (SEQ ID NO:9) | MI3 | YAP3$_{A18}$ |
| pIMI72 | MFα1(1-81)MA | Lys-Glu-Lys | MI3 | ÷ |
| pIM256 | MFα1(1-81)MA | Lys-Glu-Lys | MI3 | YAP3$_{A18}$ |
| pKV231 | MFα1(1-81)MA | Lys-Arg (comparison) | GLP-1* | ÷ |
| pKV248 | MFα1(1-81)MA | Lys (= n = 0) | GLP-1* | ÷ |

[a]K = Lys; R = Arg; E = Glu; A = Ala

In Table 1 MFαI (1-83) is the first 83 amino acids constituting the leader peptide of the Mating Factor alpha 1 precursor from *S. cerevisiae*. Residues 1–19 form the so-called pre-sequence (signal peptide) and residues 20–83 form the so-called pro-sequence (leader peptide).

MFα1(1-83) (SEQ ID NO: 1) has the amino acid sequence: Met-Arg-Phe-Pro-Ser-Ile-Phe-Thr-Ala-Val-Leu-Phe-Ala-Ala-Ser-Ser-Ala-Leu-Ala-Ala-Pro-Val-Asn-Thr-Thr-Thr-Glu-Asp-Glu-Thr-Ala-Gln-Ile-Pro-Ala-Glu-Ala-Val-Ile-Gly-Tyr-Ser-Asp-Leu-Glu-Gly-Asp-Phe-Asp-Val-Ala-Val-Leu-Pro-Phe-Ser-Asn-Ser-Thr-Asn-Asn-Gly-Leu-Leu-Phe-Ile-Asn-Thr-Thr-Ile-Ala-Ser-Ile-Ala-Ala-Lys-Glu-Glu-Gly-Val-Ser-Leu-Asp MFα1(1-81)MA is MFα1(1-83) in which the last two residues (Leu-Asp) have been substituted by Met-Ala.

MI3 is a human insulin precursor lacking amino acid residue No. 30 (B30) and having an Ala-Ala-Lys bridge connecting B29-Lys and A1-Gly of human insulin.

MI3 (SEQ ID NO: 2) has the amino acid sequence: Phe-Val-Asn-Gln-His-Leu-Cys-Gly-Ser-His-Leu-Val-Glu-Ala-Leu-Tyr-Leu-Val-Cys-Gly-Glu-Arg-Gly-Phe-Phe-Tyr-Thr-Pro-Lys-Ala-Ala-Lys-Gly-Ile-Val-Glu-Gln-Cys-Cys-Thr-Ser-Ile-Cys-Ser-Leu-Tyr-Gln-Leu-Glu-Asn-Tyr-Cys-Asn.

GLP-1* is human glucagon-like peptide GLP-1(7-37) with an extra C-terminal lysine residue and with lysine to arginine substitutions in position 26 and 34.

GLP-1* (SEQ ID NO: 3) has the amino acid sequence: His-Ala-Glu-Gly-Thr-Phe-Thr-Ser-Asp-Val-Ser-Ser-Tyr-Leu-Glu-Gly-Gln-Ala-Ala-Arg-Glu-Phe-Ile-Ala-Trp-Leu-Val-Arg-Gly-Arg-Gly-Lys For the construction of plasmids co-expressing authentic YAP3, or the C-terminal truncated YAP3 counterpart YAP$_{A18}$, DNA fragments containing the particular DNA construct were inserted into the SalI site at the 3' end of the POT gene (see FIG. 1).

The authentic YAP3 gene was derived from pME768 (Egel-Mitani et al., Yeast, 6, 1990, pp. 127–137) and encompasses 0.6 kb of the transcription-promoter sequences, and 0.3 kb of the transcription-terminator sequences.

The YAP3$_{A18}$ gene construct was derived from pME927 in which the YAP3 coding region has been truncated at the C-terminal encoding part (Egel-Mitani et al., 1990, op.cit.). The truncation makes a deletion of the last 18 codons which are replaced by two extra amino acids codons (Pro-Ile), and a UAG translation-terminal signal. Like the YAP3 gene construct, the YAP3$_{A18}$ gene construct contains the authentic 0.6 kb YAP3 gene transcription-promoter sequence but carries a 0.3 kb transcription-terminator sequence derived from the MFα1 gene.

The expression plasmids were propagated in *E. coli*, grown in the presence of ampicillin and isolated using standard techniques (Sambrook et al., 1989, op.cit.). The plasmid DNA was checked for insert by appropriate restriction endonucleases (e.g. EcoRI, XbaI and SalI) and was shown by sequence analysis to encode the proper leader/product fusion construct.

The plasmid DNA was transformed into either *S. cerevisiae* strain MT663 (MATa/MATαpep4-3/pep4-3 HIS4/his4 Δtpi::LEU2/Δtpi::LEU2) or ME1487 (MATα Δyap3::URA3pep4-3 Δtpi::LEU leu2 Δura3) as described in PCT applications No. 95/00250 and 97/00298, respectively.

Yeast transformants were selected by glucose utilization as carbon source on YDP (1% yeast extract, 2% peptone, 2% glucose) agar (2%) plates.

Quantification of secreted products by ALP digestions and HPLC

Transformants were cultivated in 5 ml. YPD liquid medium at 30° C. for 3 days with shaking at 200 rpm. Culture supernatants were collected after centrifugation at 2500 rpm. and analyzed for secreted products in the following way:

For each culture one sample (A) of 630 μl supernatant was mixed with 70 μl 1 M Tris buffer, pH 8.75, and supplied with 100 μg/ml Lys-Xaa specific *Achromobacter lyticus* protease I (ALP).

Another sample (B) of 630 μl supernatant was mixed with 70 μl 1 M Tris buffer, pH. 8.75, and without the ALP. Both samples were incubated for 2 hours at 37° C. and subsequently analyzed by HPLC.

By analyzing the B-samples (no ALP) the yield of secreted and processed product polypeptide (MI3 in Table 2 and GLP-1* in Table 3) with out attached leader could be quantified.

By analyzing the ALP-digested A-samples the yield of secreted and unprocessed pro-pre leader/product fusion (L-MI3 in Table 2 and LGLP-1* in Table 3) could be determined. ALP cleaves at the internal lysine-residues at B29 and the connecting Ala-Ala-Lys bridge. If present, ALP furthermore cleaves unprocessed leader/MI3 fusion at the lysine-residue separating the leader and MI3. Thus, the total yield of processed and unprocessed MI3 can be measured as the amount of desB30 insulin in the A-samples. The yield of unprocessed (leader-bound) MI3 can be measured indirectly by subtracting the yield of leader-free product (obtained from the B-sample) from the total yield of ALP processed product.

The yield of secreted leader-bound polypeptide could not be quantified by HPLC analysis of the sample. This was due to high amount of glycosylation (hyperglycosylation) of the pro-leader part.

However, in case of the reference-plasmid of MI3-related products, pMT742, the yield of unprocessed pro leader/MI3 fusion in the A-samples was determined directly by quantifying the amount of desB30 having an extra N-terminal arginine residue at the B-chain ("B0Arg-desB30"). B0Arg-desB30 insulin originates from a cleavage between Lys and Arg at the unprocessed kEX2 processing site.

Table 2 shows the relative yields obtained with MI3 related plasmid constructs in MT663. The yeast strain MT663 has been deposited in the Deutche Sammlung von Mikroorganismen und Zelikulturen in connection with the filing of WO92/11378 and was given the deposit number DSM 6278. This particular yeast strain has proven to be highly suitable and successful in the expression of plasmid constructs, and in the subsequent secretion of polypeptides.

TABLE 2

Relative yields obtained with MI3 related plasmid constructs in MT663.

| Plasmid | Total | MI3 | L-MI3 |
|---|---|---|---|
| PMT742 | 175[a] | 100 | 75[a] |
| PJB 162 | 290 | <1 | 290 |
| PJB 160 | 220 | 15 | 205 |
| PIM 176 | 160 | 70 | 90 |
| PIM37 | 150 | 140 | 10 |
| PIMI72 | 265 | 25 | 240 |
| PIM256 | 170 | 170 | <1 |

[a]In the case of pMT742, L-MI3 was measured as B0(Arg)-desB30 insulin relative to the yield of desB30 insulin obtained from ALP treatments of supernatants from pMT742 and the total yield was calculated as the sum of these figures.

The fermentation yields are relative to the yield of MI3 obtained with pMT742. Yields of MI3 was determined by measuring MI3 in untreated supernatants. Total yields were measured as yields of desB30 insulin in supernatants treated with ALP relative to the yield of desB30 insulin obtained from ALP treatment of supernatants from pMT742. Yields of leader bound M13 (L-MI3) were calculated by subtracting the yields of M13 from total yields.

The results in Table 2 show that constructs having a cleavage site according to the invention and no co-expressed protease (i.e. pJB162, pJB160 and plM172), produce more MI3-related product than pMT742 (i.e. 165%, 125% and 150% respectively). Moreover since leader bound MI3 (except for leader bound Arg-desB30) can be converted into desB30 insulin by ALP digestion, the yields of desB30 insulin ready to be used for the production of human insulin are thus even higher for these constructs (290%, 220% and 265%) than for the pMT742 construct. This is also true for the other constructs depicted in Table 2 (i.e. "total"=desB30 amounts). Moreover, pIM37 and pIM256 co-expressing YAP3$_{\Delta 18}$ both produce more in vivo processed MI3 than pMT742 (140% and 170% respectively). MI3 is readily usable for purification, whereas hyperglycosylated unprocessed pro-leader/MI3 fusion product is not.

TABLE 3

Relative yields obtained with glucagon like peptide GLP-1* related constructs in ME1487.

| Plasmid | GLP-1 * | L-GLP-1 * |
|---|---|---|
| PKV231 | 100 | <1 |
| PKV248 | <1 | 375 |

The fermentation yields are relative to the yield of GLP-1* obtained with pKV23I. Yields of GLP-1* was determined by measuring GLP-1* in untreated supernatants. Yields of (pro-) leader bound GLP1-1* (L-GLP1-1*) was calculated by subtracting yields of GLP-1* in untreated supernatant from yields of GLP-1* in ALP treated supernatants.

In the case of the reference-plasmid of GLP1*-related products, pKV231, unprocessed proleader/GLP1* fusion was not present since GLP1* having an extra N-terminal arginine could not be detected in the ALP-digested A-samples (Table 3). In the example of pKV248, no processed GLP1* was detected in the B-samples whereas the amount of GLP1* was found to be 375% of that obtained with pKV231 in the ALP-digested A-samples).

What is claimed is:

1. A process of making a desired polypeptide in yeast by culturing in a suitable culture medium a yeast strain containing an expression vector that expresses a sequence with the following formula $$SP\text{-}LP\text{-}X_n\text{-}PS\text{-}*polypeptide*$$

wherein

SP is a signal peptide;

LP is the native α-factor leader peptide or a leader peptide being at least 85% identical to the native α-factor leader peptide;

PS is a monobasic processing site Lys or Arg;

X is a spacer peptide containing n amino acids;

n is 0 or an integer from 1 to 10; and

*polypeptide* is the desired polypeptide;

with the proviso that the spacer peptide X is not Ile-Glu-Gly, Leu-Pro, Lys-Lys-Leu-Ile-Asp (SEQ ID NO: 4), Ile-Asp or Pro-Gly-Asp-Pro (SEQ ID NO: 5) and with the further proviso that the spacer peptide X does not contain a KEX2 cleavage site or together with PS or LP constitutes a KEX2 cleavage site and, when n=0, the C-terminal of the leader peptide is not Lys, Arg, Ile-Glu-Gly, Leu-Pro, Lys-Lys-Leu-Ile-Asp (SEQ ID NO: 4), Ile-Asp or Pro-Gly-Asp-Pro (SEQ ID NO: 5), whereupon the leader bound desired polypeptide is cleaved off at the processing site PS, either in vivo during passage through the cell membrane or in vitro after secretion into the culture medium whereupon the desired polypeptide is isolated.

2. The process according to claim 1, wherein SP is a signal peptide homologous to yeast.

3. The process according to claim 1, wherein PS is Lys.

4. The process according to claim 1, wherein X is a Lys-Glu-Ala-Glu-Ala-Glu-Ala (SEQ ID NO: 8) or Lys-Glu.

5. The process according to claim 1, wherein n is an integer from 1 to 3.

6. The process according to claim 1, wherein n=0.

7. The process according to claim 1, wherein the yeast strain contains a DNA sequence encoding a protease which is specific for a monobasic processing site, the protease is co-expressed with the leader bound polypeptide and cleaves the leader bound polypeptide at the processing site PS.

8. The process according to claim 2, wherein SP is a α-factor signal peptide, a yeast aspartic protease 3 signal peptide, a signal peptide of mouse salivary amylase, a carboxypeptidase signal peptide, or a yeast BAR1 signal peptide.

9. The process according to claim 7, wherein the co-expressed protease is trypsin, *Achromobacter lyticus* protease 1, Enterokinase, *Fusarium oxysporum* trypsin-like protease or YAP3.

10. The process according to claim 9, wherein the protease is YAP3.

11. The process according to claim 9, wherein the protease is YAP3$_{\Delta 18}$.

* * * * *